(12) United States Patent
de Heer

(10) Patent No.: US 9,375,344 B2
(45) Date of Patent: Jun. 28, 2016

(54) SYSTEMS AND METHODS FOR BREATHING ASSISTANCE

(75) Inventor: Robert de Heer, Palo Alto, CA (US)

(73) Assignee: ALL REST TECHNOLOGIES LLP, Palo Alto, CA (US)

( * ) Notice: Subject to any disclaimer, the term of this patent is extended or adjusted under 35 U.S.C. 154(b) by 149 days.

(21) Appl. No.: 12/764,046

(22) Filed: Apr. 20, 2010

(65) Prior Publication Data

US 2010/0268107 A1     Oct. 21, 2010

Related U.S. Application Data

(60) Provisional application No. 61/171,029, filed on Apr. 20, 2009.

(51) Int. Cl.
| | | |
|---|---|---|
| *A61F 5/56* | (2006.01) | |
| *A61M 16/04* | (2006.01) | |
| *A61B 5/00* | (2006.01) | |
| *A61B 5/08* | (2006.01) | |
| *A61B 7/00* | (2006.01) | |

(52) U.S. Cl.
CPC ............... *A61F 5/566* (2013.01); *A61B 5/411* (2013.01); *A61B 5/4818* (2013.01); *A61B 5/08* (2013.01); *A61B 7/003* (2013.01); *A61B 2562/0204* (2013.01); *A61M 16/049* (2014.02); *A61M 16/0488* (2013.01)

(58) Field of Classification Search
CPC ... A41D 13/05; A41D 13/11; A41D 13/1115; A41D 13/1123; A41D 13/113; A41D 13/1138; A41D 13/1146; A41D 13/1153; A41D 13/1161; A41D 13/1176; A41D 13/1184; A41D 13/1192; A41D 13/1218; A41D 2200/20; A41D 2300/32; A41D 2400/34; A41D 31/0016; A41D 31/0083; A61B 17/24; A61B 5/08; A61B 5/09; A61B 5/097; A61B 5/411; A61B 5/4818; A61C 5/14; A61F 5/56; A61F 5/566; A61M 1/00; A61M 1/0001; A61M 1/0009; A61M 1/0047; A61M 1/0052; A61M 1/0056; A61M 11/00; A61M 11/001; A61M 11/002; A61M 11/003; A61M 11/005; A61M 11/04; A61M 11/041; A61M 11/042; A61M 11/047; A61M 11/06; A61M 15/00; A61M 15/0003; A61M 15/0006; A61M 15/0015; A61M 15/0016; A61M 15/0018; A61M 15/002; A61M 15/0021; A61M 15/0023; A61M 15/0028; A61M 15/0033; A61M 15/0043; A61M 15/0045; A61M 15/0051; A61M 15/0065; A61M 15/0083; A61M 15/0085; A61M 15/0086; A61M 15/0088; A61M 15/009; A61M 15/0093; A61M 15/06; A61M 15/08; A61M 16/00; A61M 16/0006; A61M 16/0009; A61M 16/0045; A61M 16/0048; A61M 16/0051; A61M 16/0057; A61M 16/0066; A61M 16/0069; A61M 16/0078; A61M 16/0084; A61M 16/009; A61M 16/0093; A61M 16/04; A61M 16/0404; A61M 16/0409; A61M 16/042; A61M 16/0434; A61M 16/044; A61M 16/0443; A61M 16/0445; A61M 16/0452; A61M 16/0459; A61M 16/0463; A61M 16/0465; A61M 16/0468; A61M 16/047; A61M 16/0486; A61M 16/0488; A61M 16/049; A61M 16/0493; A61M 16/06; A61M 16/0611; A61M 16/0616; A61M 16/0627; A61M 16/0638; A61M 16/0666; A61M 16/0672; A61M 16/0677; A61M 16/0683; A61M 16/0688; A61M 16/08; A61M 16/0816; A61M 16/085; A61M 16/0858; A61M 16/0866; A61M 16/0875; A61M 16/10; A61M 16/1045; A61M 16/105; A61M 16/1055; A61M 16/1065; A61M 16/107; A61M 16/1075; A61M 16/108; A61M 16/109; A61M 16/1095; A61M 16/12; A61M 16/125; A61M 16/14; A61M 16/16; A61M 16/18; A61M 16/20; A61M 16/202; A61M 16/206; A61M 16/207; A61M 16/208; A61M 16/22; A62B 17/00; A62B 17/003; A62B 17/005; A62B 17/006; A62B 17/04;

A62B 17/08; A62B 18/00; A62B 18/003;
A62B 18/006; A62B 18/02; A62B 18/025;
A62B 18/04; A62B 18/08; A62B 18/082;
A62B 18/084; A62B 18/086; A62B 18/088;
A62B 18/10; A62B 19/00; A62B 19/02;
A62B 21/00; A62B 23/00; A62B 23/02;
A62B 23/025; A62B 23/06; A62B 25/00;
A62B 27/00; A62B 29/00; A62B 33/00;
A62B 7/00; A62B 7/02; A62B 7/08; A62B
7/10; A62B 7/12; A62B 9/00; A62B 9/003;
A62B 9/006; A62B 9/02; A62B 9/04; A62B
9/06; A62B 99/00; B01D 29/01; B01D
29/012; B01D 29/07; B01D 29/11; B01D
29/111; B01D 29/21; B01D 29/213; B01D
39/16; B01D 39/1623; B01D 39/18; B01D
39/20; B01D 39/2024; B01D 46/0031; B01D
46/02; B01D 46/2411; B01D 46/52; B01D
46/521
USPC ............... 128/848, 859–861, 200.24, 200.26,
128/201.211, 201.26, 202.28, 205.27,
128/205.29, 206.29, 207.14, 200.29,
128/201.11, 201.25, 201.28, 202.13,
128/203.21, 204.13, 204.23, 205.13,
128/205.24, 205.25, 205.28, 206.11,
128/206.12, 206.15, 206.16, 206.17,
128/206.19, 206.21, 206.24, 206.27,
128/206.28, 207.11, 207.12, 207.13,
128/207.16, 207.17, 207.18, 207.29, 842,
128/857, 862, 863, 909; 600/239, 529, 538,
600/539; 604/131, 268, 275, 319, 328, 35,
604/73
See application file for complete search history.

(56) References Cited

U.S. PATENT DOCUMENTS

| | | | | |
|---|---|---|---|---|
| 3,057,347 | A * | 10/1962 | McGee | 128/202.28 |
| 3,858,573 | A * | 1/1975 | Ryan et al. | 600/543 |
| 4,231,364 | A * | 11/1980 | Speshyock | 128/206.15 |
| 4,662,367 | A * | 5/1987 | Gore, Jr. | 128/202.28 |
| 4,719,911 | A * | 1/1988 | Carrico | 128/206.29 |
| 5,020,529 | A * | 6/1991 | Gobin | 128/202.28 |
| 5,086,768 | A * | 2/1992 | Niemeyer | 128/205.24 |
| 5,315,987 | A * | 5/1994 | Swann | 128/201.28 |
| 5,386,825 | A * | 2/1995 | Bates | 128/205.27 |
| 5,394,867 | A * | 3/1995 | Swann | 128/201.25 |
| 5,552,048 | A * | 9/1996 | Miller et al. | 210/489 |
| 5,611,332 | A * | 3/1997 | Bono | 128/200.18 |
| 5,630,409 | A | 5/1997 | Bono et al. | |
| 5,647,345 | A | 7/1997 | Saul | |
| 5,782,234 | A * | 7/1998 | Bates | 128/205.27 |
| 6,010,458 | A * | 1/2000 | Roberts | 600/529 |
| 6,244,865 | B1 * | 6/2001 | Nelson et al. | 433/140 |
| 6,758,212 | B2 * | 7/2004 | Swann | 128/201.25 |
| 6,981,502 | B2 * | 1/2006 | McCormick et al. | 128/206.29 |
| 7,025,060 | B1 * | 4/2006 | Nicholson | 128/206.29 |
| 2005/0133024 | A1 | 6/2005 | Coifman | |
| 2006/0112962 | A1 | 6/2006 | Tebbutt et al. | |
| 2006/0137689 | A1 * | 6/2006 | Evensson | 128/205.27 |
| 2006/0225738 | A1 | 10/2006 | Afentoulopoulos | |

OTHER PUBLICATIONS

PCT International Search Report and Written Opinion dated Jun. 29, 2010 for International Application No. PCT/US2010/031812, 8 pages.

Sleep apnea device is small enough to fit in your wallet, published Published: Tuesday, Feb. 28, 2012 [Online] [retrieved May 14, 2013] retrieved from: http://www.cleveland.com/healthfit/index.ssf/2012/02/new_device_to_treat_sleep_apne.html.

* cited by examiner

*Primary Examiner* — Annette Dixon

(74) *Attorney, Agent, or Firm* — Hogan Lovells US LLP

(57) ABSTRACT

Various embodiments provide for a breathing assistance device comprising right and left flanges and a protuberance. The right and left flanges may comprise an inner surface and an outer surface, and the flanges may be configured to be placed in a user's mouth such that at least a portion of the flanges are in front of teeth of the user. The protuberance may extend from the outside surface of the flanges and may define an air passage that passes through the flanges.

10 Claims, 9 Drawing Sheets

SYSTEMS AND METHODS FOR BREATHING ASSISTANCE

CROSS-REFERENCE TO RELATED APPLICATION

The present application claims benefit of U.S. Provisional Patent Application No. 61/171,029 filed Apr. 20, 2009, and entitled "Systems and Methods for Breathing Assistance" which is incorporated herein by reference.

BACKGROUND

1. Field of the Invention

The present invention generally relates to breathing assistance. More particularly, the invention relates to systems and methods for breathing assistance.

2. Description of Related Art

Sleep disorders are increasingly common. Sleep problems may cause more than just sleepiness. A lack of sleep may affect relationships, health, mood (people with sleep apnea are 5 times more likely to suffer from depression), and mental acuity. As a result, personal and professional relationships may suffer. Further, a lack of quality sleep may be related to misjudgments and accidents.

Sleep apnea is a common sleep disorder that can be potentially serious. When a sleeper has sleep apnea, their breathing may stop or get very shallow during sleep. Each pause in breathing may typically last 10 to 20 seconds or more and the pauses may occur 20 to 30 times or more an hour. During episodes of apnea, the sleeper may wake up to breathe again. As a result, sleep is disrupted and the sleeper may suffer from a brief lack of oxygen.

Those with sleep apnea may use a Continuous Positive Airway Pressure (CPAP) machine. A CPAP machine delivers a stream of compressed air via a hose to a nasal pillow, nose mask, or full-face mask. The airway is split (keeping airway open under air pressure) so that unobstructed breathing becomes possible. The CPAP machine blows air at a prescribed pressure. The necessary pressure is usually determined by a sleep physician after review of a sleep study that is supervised by a sleep technician in a sleep laboratory.

Unfortunately, both the CPAP machine and the sleep study tend to be very expensive. Further, CPAP machines are noisy which may interrupt or prevent sleep of the user or other family members. Moreover, many users have trouble sleeping with a nasal pillow, nose mask, or full-face mask.

SUMMARY OF THE INVENTION

Systems and methods for breathing assistance are discussed. In various embodiments, a breathing assistance device comprises right and left flanges and a protuberance. The right and left flanges may comprise an inner surface and an outer surface. Further, the flanges may be configured to be placed in a user's mouth, wherein at least a portion of the flanges are in front of teeth of the user. The protuberance may extend from the outside surface of the flanges. Further, the protuberance may define an air passage that passes through the flanges.

In some embodiments, the breathing assistance device may comprise a polymer. The flanges may be canted. In various embodiments, a filter that is configured to limit air resistance is within the protuberance. The filter may comprise a varnished material. The breathing assistance device my further comprise a filter ridge within the protuberance wherein the filter ridge is configured to restrain the filter.

In various embodiments, when the breathing assistance device is formed, a frenulum gap along a y axis is created. The frenulum gap may be configured to allow a user's frenulum to be within the frenulum gap.

The protuberance may extend from the outside surface at an angle. In some embodiments, the left and right flanges comprise edges which are configured to contact gums of the user.

An exemplary method comprises forming right and left flanges comprising an inner surface and an outside surface, the flanges configured to be placed in a user's mouth, wherein at least a portion of the flanges are in front of teeth of the user, and forming a protuberance extending from the outside surface of the flanges, the protuberance defining an air passage that passes through the flanges.

Another exemplary method comprises selecting a filter for a breathing assistance device comprising right and left flanges comprising an inner surface and an outside surface and a protuberance extending from the outside surface of the flanges, the protuberance defining an air passage that passes through the flanges, placing the filter in the protuberance of the breathing assistance device, and placing a breathing assistance device within a mouth of a user, the breathing assistance device configured to assist the user's breathing.

BRIEF DESCRIPTION OF THE DRAWINGS

FIG. 10 is a left side view of an exemplary breathing assistance device comprising a protuberance extending from the outside surface of the breathing assistance device at an angle.

DETAILED DESCRIPTION OF THE INVENTION

A breathing assistance device may be used to assist a user with breathing problems. In various embodiments, the breathing assistance device may be used to relieve sleep apnea. There are at least two different types of sleep apnea, including obstructive sleep apnea and central sleep apnea. Obstructive sleep apnea is caused by an obstruction of the airway. For example, the soft tissue of the airway may collapse thereby obstructing sleep. Central sleep apnea, or Cheyne-Stokes, is caused by the brain's respiratory control centers being imbalanced during sleep. As a result, the body does not react quickly enough during sleep to maintain an even respiratory rate, thereby causing the body to cycle between apnea and hyperpnea.

In order to alleviate one or more of these problems, a user may place the breathing assistance device in their mouth prior to sleep. The breathing assistance device may hold the teeth of the user open allowing for greater air flow. Further, a protuberance of the breathing assistance device may extend past the user's lips allowing air to pass through the breathing assistance device into the user's mouth. The removal of obstacles to air flow in this manner may reduce or eliminate sleep apnea. For example, the greater air flow may reduce negative air pressure in the mouth which may help to keep soft tissue in the airway from collapsing. Further, the greater air flow may allow the user's body to more easily maintain an acceptable respiratory rate which may reduce or eliminate the cycle between apnea and hyperpnea.

Figure 1:
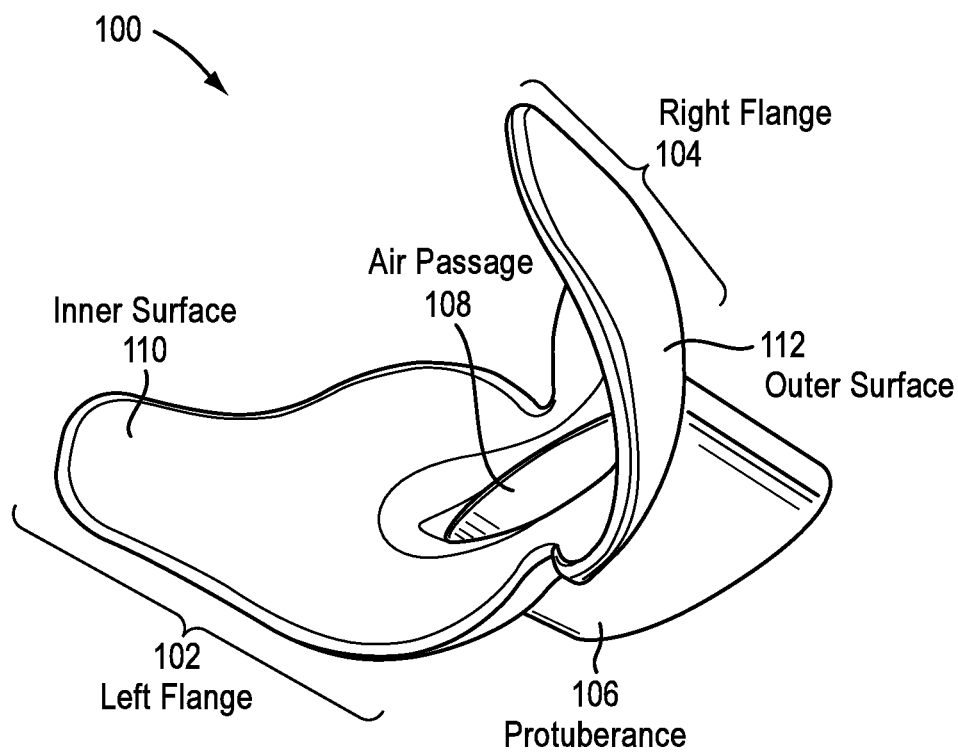
FIG. 1 is a perspective view of an exemplary breathing assistance device.

FIG. 1 is a perspective view of an exemplary breathing assistance device 100. The breathing assistance device 100 comprises a left flange 102, a right flange 104, and a protuberance 106. The protuberance 106 is hollow and defines an air passage 108 that allows air flow through the breathing assistance device 100. The surface of the left and right flanges 102 and 104 that is opposite the protuberance 106 is the inner surface 110. The surface of the left and right flanges 102 and 104 that is on the same side as the protuberance 106 is the outer surface 112.

In various embodiments, the breathing assistance device 100 may be used similar to a mouth guard. For example, the user may place the breathing assistance device 100 in the mouth with the protuberance 106 extending beyond the user's lips. The flanges 102 and 104 may extend along the inside of the user's cheeks and may be at least partially in front of the user's teeth. The inner surface 110 may be facing the user's mouth and the outer surface 112 may be touching or at least partially touching the cheeks and/or lips of the user. In some embodiments, the breathing assistance device 100 holds the user's jaw forward to increase airflow.

The user can orient the breathing assistance device 100 so that saliva is less likely to flow through the air passage 108, while the user is sleeping on their side. For example, the user may slide the breathing assistance device 100 to the upper portion of the mouth.

The flanges 102 and 104 prevent the breathing assistance device 100 from being too loose or accidentally falling out of place. The inside surface 110 of the flanges 102 and 104 may be curved. The curved surface of the flange may be configured to hold the air passage 108 in or around the correct location to assist the user in breathing air through the air passage 108. In one example, the inside surface 110 is concave so that the flanges 102 and 104 do not press on the teeth of the user. In some embodiments, the inside surface 110 of the flanges 102 and 104 is flat. The length, height, and thickness of the flanges 102 and 104 may be configured to keep the breathing assistance device 100 comfortably in place.

The flanges 102 and 104 may be any length and height. In one example, the flanges 102 and 104 are similar to flanges found on mouth pieces in scuba equipment. The flanges 102 and 104 may range, for example, from ¼ inch to ½ inch and the height of the flanges 102 may range from ¼ inch to 1¾ of an inch. In some embodiments, the flanges 102 and 104 may be thick enough to lightly push against the lips of the user to encourage the user's mouth naturally open and reduce bruxism.

In various embodiments, the protuberance 106 and the air passage 108 are located in the center of the breathing assistance device 100. Those skilled in the art will appreciate that the protuberance 106 may be located at any place of the breathing assistance device 100. In some embodiments, the protuberance 106 is flexibly coupled to the breathing assistance device 100 allowing the protuberance 106 to bend in different directions.

The protuberance 106 extends from the flanges 102 and 104. In various embodiments, the protuberance 106 holds the lips of the user open. In one example, the protuberance 106 extends through the lips allowing the user's lips to rest along a portion of the protuberance 106. In another example, the protuberance 106 does not extend through the user's lips, but rather extends from the flanges 102 and 104 sufficiently so that the user's lips are held open to allow air to pass through the air passage 108. Although FIGS. 1-7 depict the protuberance 106 as oval, the protuberance 106 may be any shape. The protuberance 106, may, for example, be round, rectangular, or trapezoidal.

Although the protuberance 106 and air passage 108 are depicted as extending directly away from the flange 108, those skilled in the art will appreciate that the protuberance 106 and air passage 108 may be constructed at an angle. For example, the protuberance 106 and air passage 108 may be tilted. In one example, the protuberance 106 and air passage 108 may be tilted away from the flange 108 and upwards towards the user's nose. The protuberance 106 and air passage 108 may be tilted in any direction. In some embodiments, the breathing assistance device 100 is constructed from a material that allows the user to direct the angle of the protuberance 106 and air passage 108.

The protuberance 106 may be at any length extending from the flanges 102 and 104. In one example, the protuberance 106 extends ½ inch from the flanges 102 and 104. In another example, the protuberance 106 extends 1½ inches from the flanges 102 and 104. The protuberance 106 may extend anywhere from ½ inch to 1½ inches from the flanges 102 and 104. Those skilled in the art will appreciate that the protuberance 106 may be any length.

The protuberance 106 defines the air passage 108. The air passage 108 allows for the passage of air into the mouth of the user. It will be appreciated by those skilled in the art that the air passage 108 may be any shape and comprise a plurality of passages from which air may flow into the user's mouth. In some embodiments, the air passage 108 is wide enough to permit increased air flow during an inspiratory gasp response breathing episode. In some embodiments, the breathing assistance device 100 may be considered optimized when the air flow capacity of the device is slightly less than or equal to the user's natural breathing capacity.

In some embodiments, the protuberance 106 may be coupled to a retainer device that is formed to the shape of the user's upper or lower teeth. Alternatively, the protuberance 106 may be coupled to anchors that are cemented to the teeth.

The breathing assistance device 100 may also comprise one or more holes in or next to the protuberance 106 that allow air to flow in and out of the user's mouth. In some embodiments the one or more holes next to the protuberance 106 allow saliva to flow out of the user's mouth.

In some embodiments, the protuberance 106 comprises a mesh or perforated material at one end of the air passage 108. In one example, a mesh is located across any air passages 106 in the breathing assistance device 100. The mesh may allow for air to enter into the air passage 108 but prevents debris (e.g., bugs or dust) from getting within the air passage 108.

In various embodiments, an air filter may be fitted into the protuberance 106. The air filter may allow for limited air resistance within the protuberance 106. In one example, a user may breathe air through the air filter within the protuberance 106. The air resistance through the air filter may be such that a level of warmth, humidity, and/or positive air pressure is maintained within user's mouth while using the breathing assistance device 100.

The breathing assistance device 100 may comprise any kind of material and be of any hardness. In some embodiments, the breathing assistance device 100 comprises a Shore A hardness with a durometer value between 30 OO and 75 D. The breathing assistance device 100 may comprise a polymer such as an elastomer and may be food safe. In one example, the breathing assistance device 100 may be a thermo-plastic elastomer, silicon material, foam material or any combination. Examples of elastomers include, but are not limited to, rubber, synthetic polyisoprene, bytul rubber, polybutadiene, styrene-butadience rubber, nitrile rubber, cloroprene rubber, ethylene propylene rubber, ethylene propylene diene rubber, epichlorohydrin rubber, polyacrylic rubber, silicone rubber, fluorosilicone rubber, fluoroelastomers viton, tecnoflon, fluorel, alias and Dai-El, perfluoroelastomers tecnoflon PIR, kalrez, chemraz, and perlast, polyether block amides, chlorosulfonated polyethylene, ethylene-vinyl acetate, Thermoplastic elastomers (e.g., elastron), thermoplastic vulcanizates (e.g., santoprene TPV), thermoplastic polyurethane, thermoplastic olefins, proteins resilin and elastin, and polysulfide rubber.

The breathing assistance device 100, as described in many of the embodiments described here, may be made of a soft material that allows the device to flex as the user's mouth moves.

The breathing assistance device 100 may be shaped differently than that depicted in FIG. 1. For example, the breathing assistance device 100 may comprise a teeth separator (e.g., bite guard) extending from the flange 102 and 104 in a direction away from the protuberance 106. The teeth separator may be a ridge of material that fits between the teeth to keep the teeth apart (e.g., the teeth may rest on the teeth separator) thereby improving air flow and/or reducing bruxism (i.e., teeth grinding). The teeth separator may comprise a single piece of material that extends from the left flange 102, across the air passage 108, to the right flange 104. Alternatively, the teeth separator may comprise two pieces or more of material, each piece extending along at least a portion of a flange 102 or 104 without being over the air passage 108. The teeth separator may be of any shape and angled (e.g., angled upwards towards the user's upper jaw, or angled downwards). The teeth separator may have any thickness. For example, the teeth separator may be from ¼ inch thick to ⅝ inch thick. FIG. 10 is a left side view 1000 of an exemplary breathing assistance device comprising a protuberance 1006 extending from an outside surface 1012 of the breathing assistance device at an upward angle. The left side view 1000 displays a left flange of the exemplary breathing assistance device.

In some embodiments, the breathing assistance device 100 optimizes or substantially optimizes esophageal pressure by creating an amount of aerodynamic drag in the protuberance/filter assembly. Esophageal pressure is created naturally by the sinuses when a user breathes through their nose. The sinuses create air resistance by roughly 50%. Esophageal air pressure causes the sinuses to release Nitric. Oxide, (NO). NO causes the lungs to expand, thus facilitating respiration. The amount of NO released by the sinuses increases with the amount of esophageal pressure.

An exemplary approach to optimizing/calibrating the breathing assistance device 100 for a specific user is to measure esophageal pressure concurrently with general sleep architecture. In some embodiments, the optimal or substantially optimal pressure measurement is universal, so the breathing assistance device 100 may be calibrated for a specific user based on an esophageal pressure measurement. In some embodiments, a filter with one optimal or substantially optimal resistance measurement may work for any user, thus obviating the need for calibration.

In some embodiments, the breathing assistance device 100 is specifically created by a specialist to fit a specific user. In other embodiments, the breathing assistance device 100 may be available over retail. In one example, there may be different sizes to fit different people with different needs (e.g., one model for children, one model for men, and another model for women).

In various embodiments, the breathing assistance device 100 could improve oxygenation and/or help avoid hypoxia. As a result, the breathing assistance device 100 may relieve or reduce the discomfort of symptoms related to respiratory diseases and conditions including common cold, flu, bronchitis, allergies, drunkenness, unconsciousness due to head wounds or unconsciousness such as after surgery or anesthetization, neck and spinal injuries that might interfere with proper breathing, digestive diseases and conditions that may interfere with lung expansion such as candida overgrowth, and/or gas/bloating.

Figure 2:
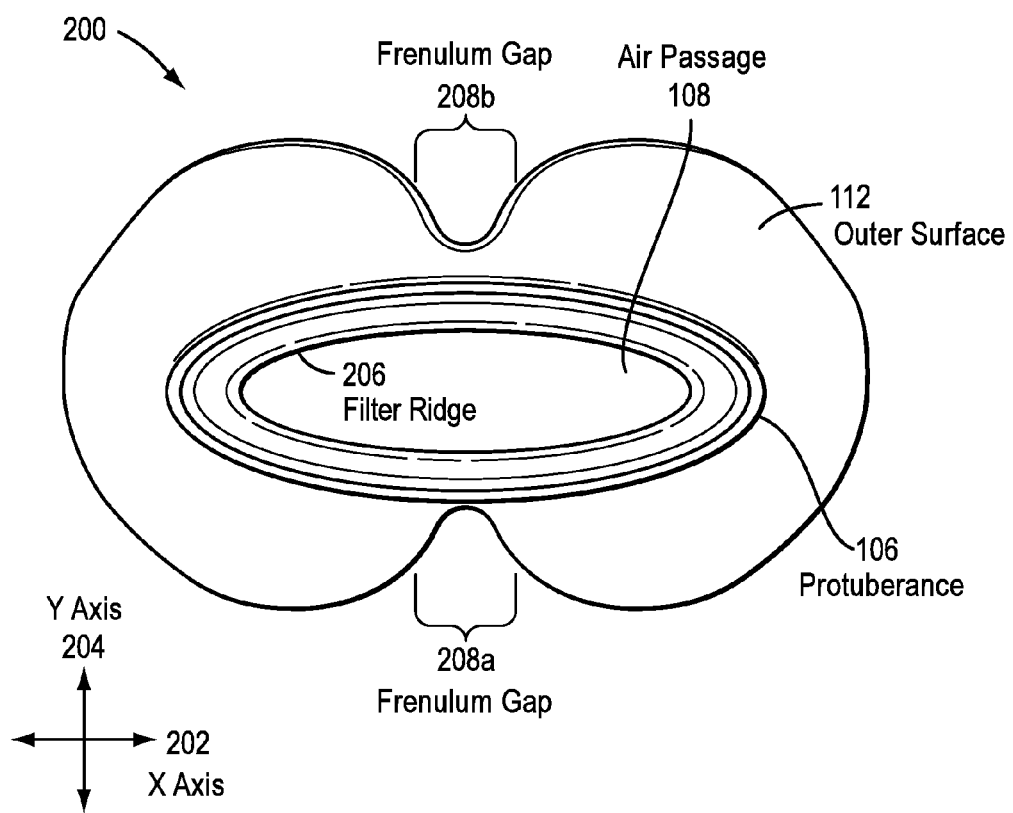
FIG. 2 is a front view of the exemplary breathing assistance device.

FIG. 2 is a front view 200 of the exemplary breathing assistance device 100. An x axis 202 and a y axis 204 have been depicted for convenience of orientation. The front view 200 of the breathing assistance device 100 depicts the air passage 108 through the protuberance 106. The filter ridge 206 and the frenulum gaps 208a and 208b are also depicted.

The filter ridge 206 is a ridge in the back of the protuberance 106. The back of the protuberance 106 is that portion of the protuberance 106 that is closest to the flanges 102 and 104. The filter ridge 206 extends from the protuberance 106 into the air passage 108. In various embodiments, a filter may be placed within the air passage 108 of the protuberance 106. The filter ridge 206 may keep the filter in place and prevents the filter from slipping through the back of the protuberance 106. The filter ridge 206 may keep a gap between the filter and the user's teeth. In some embodiments, the gap between the filter and the user's teeth is 1 mm. In various embodiments, the gap may be 1 mm to 1 cm. Those skilled in the art will appreciate that the gap may be any size.

In some embodiments, a user may select a filter to place within the protuberance 106. The user may have a selection of different filters. Filters may be of different sizes. In one example, the size of the appropriate filter may depend on the size of the breathing assistance device 100. In another example, the size of the filter may be based on preference and/or needs of the user. A user with healthy lungs may require a filter of sufficient size to allow for the desired properties of the breathing assistance device 100 (e.g., temperature, humidity, and air pressure as discussed herein). A user with weaker lungs may require a smaller filter and/or a filter composed of different materials.

The filter may be of any material. In various embodiments, the filter may comprise a roll of varnished (e.g., with shellac), corrugated paper. The varnish may be of any type including resin, alkyd, drying oil, polyurethane, lacquer, or acrylic. In some embodiments, the filter may comprise cloth or mesh. The air filter may be fabricated or manufactured out of any kind of material suitable for creating limited air resistance. In one example, the filter comprises small balls of soft paper fiber that are coupled together to form a porous structure. In another example, the filter is made out of paper or plastic honeycomb material.

Those skilled in the art will appreciate that filter may be made out of many different materials. In one example, the filter may be made of thread, including but not limited to hemp or cotton. The thread may or may not be coated with a varnish. In another example, the filter may be comprised of a fibrous material, such as Polyfiber from HBH Pet Products. In some embodiments, the filter may be constructed from an extruded material such as plastic, or paper pulp coated with a varnish. In other embodiments, the filter may be comprised of a metal wool material, such as stainless steel wool. The filter may also be constructed of strips of foam rolled into the shape of the protuberance. In some embodiments, the filter comprises reticulated foam. Open space could be created between the layers of the foam with spacers to optimize airflow through the filter.

The filter may be disposable after each use, or may be constructed in a way that it can be cleaned and reused.

The filter may comprise one or more holes that allow saliva to be forced out by air pressure. The holes of the filter may be of any diameter. For example, the holes of the air filter may be as small as 1 mm. If there are multiple holes, the sum of the holes may correlate to the user's lung strength as discussed herein.

The filter may be of any thickness. In one example, the filter is between 1/8 inch thick and 3/4 inch thick. The thickness of the filter may depend upon the user's lung strength. In various embodiments, the user may select from a variety of filters of different thicknesses and/or materials based on lung strength. The filter may be of any height. In one example, the filter is between 5 mm to 20 mm in height. The height of the filter may depend upon the user's lung strength.

In some embodiments, the filter may be comprised of a valve that allows the user to adjust the airflow to a custom/prescribed level.

In various embodiments, the user may select a filter based on the user's lung strength. For example, a user may measure their lung strength with a spirometer. A separate filter and/or breathing assistance device 100 may be recommended depending on the measurement of the spirometer. For example, a user may measure lung performance between 525 to 550 L/Min without a filter. Based on this information, the user may consult instructions or be recommended a filter that provides 5 to 10% greater air resistance.

After testing one or more times, the user may select and/or modify a filter so that the filter has the desired physical characteristics (e.g., select a filter with the desired materials and with the desired thickness).

Those skilled in the art will appreciate that, in some embodiments, the filter ridge 206 is optional and the filter may be coupled to the front or back of the protuberance 106.

In various embodiments, the filter is made of the same material as the breathing assistance device 100. In one example, the filter is an insert that fits into the air passage 108. The insert may have a hole (e.g., 15/32" diameter) in the middle of the insert. The insert may create resistance in the airway. In some embodiments, a porous filter material can be placed on the inside or outside of the insert to reduce the loss of humidity while breathing.

Those skilled in the art will appreciate that the filter may be built into the breathing assistance device 100 such that the filter is not removable. Alternately, the user, retailer, or professional may insert the filter into the breathing assistance device 100.

The frenulum gaps 208a and 208b are gaps at the top and bottom of the breathing assistance device 100 between the left flange 102 and the right flange 104. A user's frenulum (i.e., the frenulum labii superioris inside the upper lip and the frenulum labii inferioris inside the lower lip) may fit between the frenulum gaps 208a and 208b, respectively. In some embodiments, the frenulum gaps 208a and 208b allow for a comfortable fit within a user's mouth. In one example, the user's frenulum is able to move between the frenulum gaps 204a and 204b. The frenulum gaps 208a and 208b may be of any shape.

The upper frenulum gap 208a is along y axis 204 above x axis 202. The lower frenulum gap 208b is along the y axis 204 below x axis 202. In various embodiments, there may be no upper frenulum gap 208a and/or no lower frenulum gap 208b.

Figure 3:
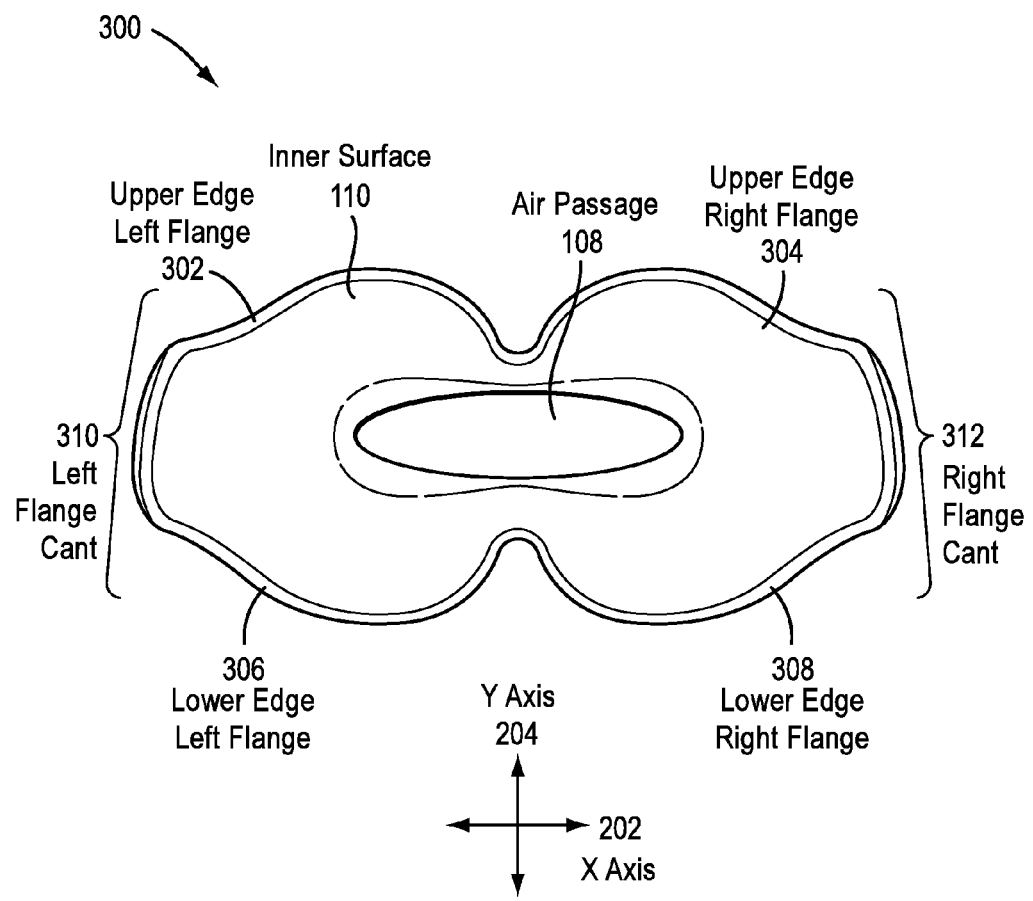
FIG. 3 is a back view of the exemplary breathing assistance device.

FIG. 3 is a back view 300 of the exemplary breathing assistance device. An x axis 202 and a y axis 204 have been depicted for convenience of orientation. The back view 300 of the breathing assistance device 100 depicts the air passage 108 through the protuberance 106. The upper portion of right flange 102 and the upper portion of left flange 104 are above the x axis 202. The lower portion of the right flange 102 and the lower portion of the left flange 104 are below the x axis.

In some embodiments, the curvature of the edge of the upper right flange 102 (i.e., the upper edge right flange 304) and/or the curvature of the edge of the upper left flange 104 (i.e., the upper edge left flange 302) may be curved less than the curvature of the edge of the lower right flange 102 (i.e., lower edge right flange 308) and/or the curvature of the edge of the lower left flange 104 (i.e., lower edge left flange 306). In other embodiments, the curvature of the upper edge right flange 304 and/or the upper edge left flange 302 may be curved more than the curvature of the edge of the lower edge right flange 308 and/or the lower edge left flange 306. In still other embodiments, the curvature of the upper edge right flange 304 and/or the upper edge left flange 302 may be substantially similar to the curvature of the edge of the lower edge right flange 308 and/or the lower edge left flange 306.

In various embodiments, the left flange 102 and the right flange 104 may have a cant (e.g., the left flange 102 and the right flange 104 may be angled or flared) such that the breathing assistance device 100 fits more comfortably in a user's mouth. In one example, the end of the left flange 102 that is opposite the protuberance 106 may be angled to create the cant (i.e., the left flange cant 310). Similarly, the end of the right flange 104 that is opposite the protuberance 106 may be angled to create a cant (i.e., the right flange cant 312). In some embodiments, the flanges 102 and 104 of the breathing assistance device 100 may be independently adaptable by the user so that the user can create the desired cants. The cants 310 and 312 may allow for the lower jaw to have more latitude to move. The cant may be of any angle. In some embodiments, the cants 310 and 312 are above 3 degrees. In various embodiments, the cants 310 and 312 have an angel from 1 to 10 degrees. Those skilled in the art will appreciate that the degree of angle of cant 310 may not be equal to the angle of cant 312. In some embodiments, one or both of the flanges 102 and 104 do not have a cant.

In some embodiments, the upper and lower edges of the breathing assistance device 100 help to keep the user's teeth along the upper and lower jaw open. By keeping the teeth from clenching, the breathing assistance device 100 may reduce grinding. In one example, the upper edge left flange 302, the upper edge right flange 304, lower edge left flange 306, lower edge right flange 308 may gently press against the user's upper and lower gums; the pressure may increase if the user attempts to close their mouth. As a result, the mouth and/or space between the teeth may be naturally kept slightly open during sleep thereby allowing greater airflow and reduction of negative pressure in the mouth. Further, the open airway may keep the uvula of the user from vibrating.

Figure 4:
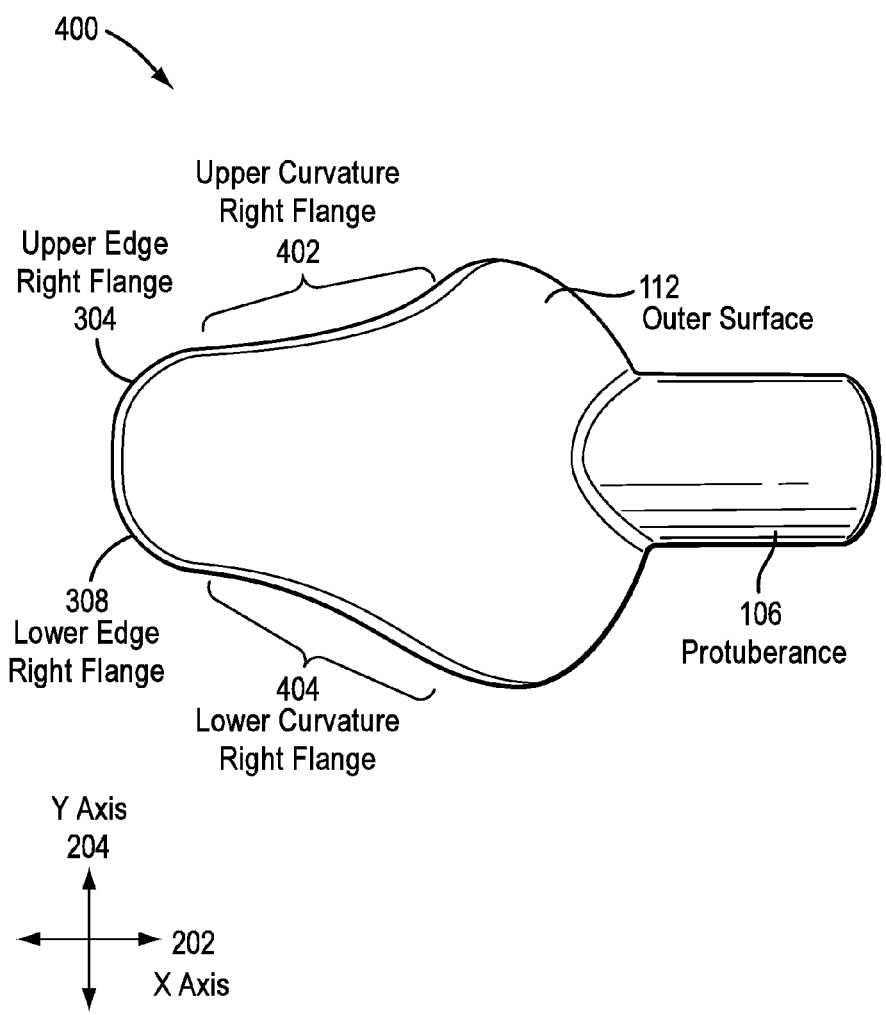
FIG. 4 is a right side view of the exemplary breathing assistance device.

FIG. 4 is a right side view 400 of the exemplary breathing assistance device 100. The right side view 400 displays the right flange 104 as well as the protuberance 106. The curvature of the outer surface 112 of the flange 104 may be of any degree. In some embodiments, the outer surface 112 of the right flange 104 is curved such that the top and bottom edge of the right flange 104 may come in contact with the gums or teeth of the user while the rest of the right flange 104 does not contact the user's teeth. Further, the curvature may be such that the lips of the user rest easily against at least a portion of the outer surface. FIG. 4 also depicts the upper curvature of the right flange 402 as well as the lower curvature right flange 404.

In some embodiments, the breathing assistance device 100 is symmetrical about the x axis 202. In one example, the top portion of the right flange 104 above the x axis 202 is similar to the bottom portion of the right flange 104 below the x axis. In other embodiments, the top portion of the right flange 104 above the x axis 202 is not similar to the bottom portion of the right flange 104 below the x axis 202.

In various embodiments, the breathing assistance device 100 may be coupled to one or more other devices. In one example, the protuberance 106 may be coupled with a humidifier that moistens air that flows through the air passage 108. In another example, the protuberance 106 may be coupled with a dehumidifier, nebulizer, and/or other device.

Alternately, the breathing assistance device 100 may be coupled to a suction device. In some embodiments, the protuberance 106 is coupled to a suction device that applies negative pressure to the airway. In one example, the nasal passages may be plugged to create suction in the mouth. The negative pressure may increase the amount of air that the user exhales. Improved exhalation improves the extraction of $CO_2$ from the lungs and increases oxygen flow into the lungs. Poor breathing can lead to conditions such as metabolic acidosis which can lead to coma or death.

In various embodiments, the breathing assistance device 100 is coupled to a device that monitors (i.e., a monitoring device) the user's breathing cycles and applies positive and negative pressure at the appropriate times to extend breathing cycles. In one example, a tube from the monitoring device may be coupled to the protuberance 106. When the user exhales, the monitoring device may apply a negative pressure to assist the user in exhalation. When the user inhales, the monitoring device may apply a positive pressure to assist the user in inhalation. Those skilled in the art will appreciate that, in some embodiments, the monitoring device only monitors the breathing assistance device 100 and does not apply either negative or positive pressure. In some embodiments, the monitoring device only applies negative pressure or only applies positive pressure.

The device may be designed in such a way that the airway dynamically adjusts to optimize how air flows in and out of the user's mouth during breathing cycles. In one example, the protuberance 106 may be designed with valves that constrict when the user inhales or exhales. For example, the valves may collapse or expand when air flows in a specific direction.

In some embodiments, the breathing assistance device 100 is coupled to a monitor device that is configured to detect when the user's blood oxygenation level drops below a configured level. When the monitor device detects a low oxygen event, a stimulus may be delivered to awaken the user. For example, the stimulus may comprise an audible event such as an alarm buzzer or radio, a physical sensation such as a prodding or vibration, and/or an olfactory sensation such as a pleasant scent, an invigorating scent, or a chemical stimulant delivered via the nose.

A training device may also be coupled to the breathing assistance device 100. The training device is configured to monitor the user's breathing and to apply a stimulus to train or encourage the user to breath at regular intervals. In one example, the training device may apply negative and positive pressure in intervals designed to adjust the user's breathing during sleep. This embodiment may treat a common symptom of sleep apnea where the user fails to initiate breathing at regular intervals and then takes a deep quick breath (i.e., an inspiratory gasp response breath).

Figure 5:
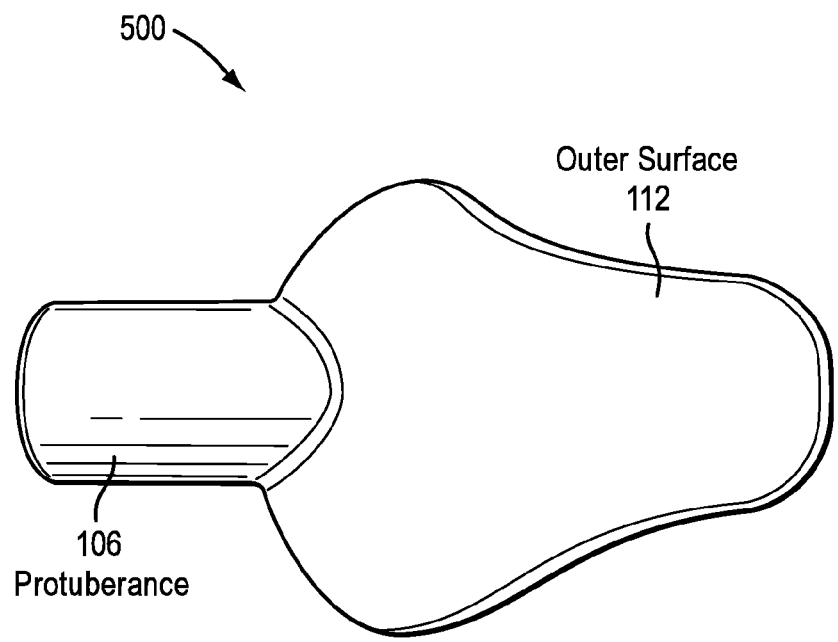
FIG. 5 is a left side view of the exemplary breathing assistance device.
Figure 5:
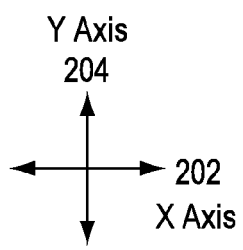

FIG. 5 is a left side view 500 of the exemplary breathing assistance device 100. The left side view 500 displays the left flange 102 as well as the protuberance 106. Similar to the right flange 102, the curvature of the outer surface 112 may be of any degree. The outer surface of the left flange 102 is curved such that the top and bottom edge of the left flange 102 may come in contact with the gums or teeth of the user while the rest of the right left flange 102 does not contact the user's teeth. Further, the curvature may be such that the lips of the user rest easily against at least a portion of the outer surface.

The top portion of the left flange 102 above the x axis 202 may be similar to the bottom portion of the left flange 102 below the x axis 202. In other embodiments, the top portion of the left flange 102 above the x axis is not similar to the bottom portion of the left flange 102 below the x axis 202.

Further, the breathing assistance device 100 may be symmetrical across the y axis 204. For example, the left flange 102 may be similar to the right flange 104. In other embodiments, the left flange 102 may be dissimilar to the right flange 104.

Figure 6:
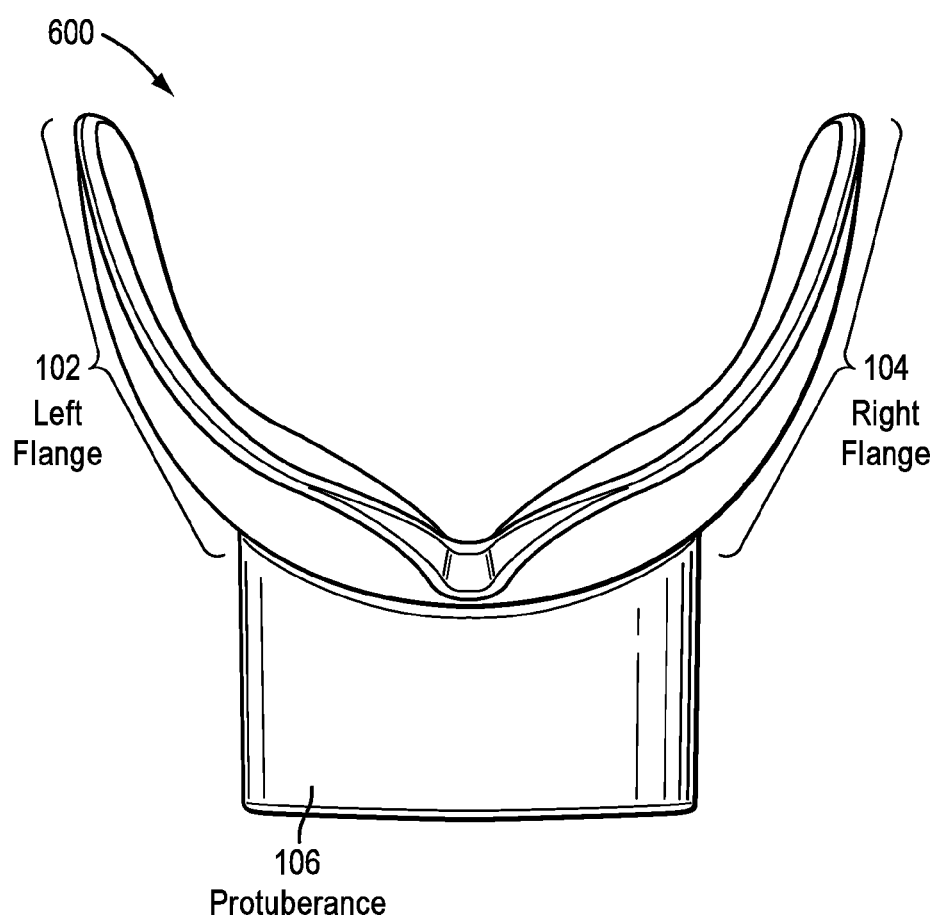
FIG. 6 is a top view of the exemplary breathing assistance device.

FIG. 6 is a top view 600 of the exemplary breathing assistance device 100. From the top view 600, the lower portion of the inside surface 110 of the breathing assistance device 100 is viewable because of the cant of the left flange 102 and the cant of the right flange 104.

In some embodiments, the breathing assistance device 100 may be held on the user's head with a head strap to limit or eliminate shifting during sleep. The strap may also improve the seal between the user's mouth and the device. In another example, the head strap is configured to hold all or a portion of the breathing assistance device 100 in place outside of the user's mouth.

In various embodiments, the breathing assistance device 100 is configured to hold the user's jaw in a forward position. In one example, a teeth separator is configured to push out the user's jaw and additional airflow is allowed to pass (e.g., through air holes). In another example, the teeth separator is configured to push out the user's jaw and the flange 108 is reduced or eliminated to allow additional air flow into the mouth.

A pillow may also be used to assist in the user's breathing. For example, a user may use the breathing assistance device 100 and a pillow that allows for a more comfortable and/or efficient positioning of the neck and head. In some embodiments, the pillow allows the user to sleep on their side and to tilt their head back. The pillow may also allow the user to rotate their head slightly in a more upwards position.

Those skilled in the art will appreciate that the user may use the breathing assistance device 100 in conjunction with various sleeping aides including, but not limited to, sleeping pills and/or sedatives. Without the breathing assistance device 100, patients who suffer from sleep apnea may not be able to take sleeping pills because the medication may further disrupt healthy breathing patterns. Since breathing assistance device 100 holds the airway open, the breathing assistance device 100 may reduce or eliminate the threat of improper breathing.

A sensor may be added to the breathing assistance device 100. In various embodiments, the sensor detects audio events. In some embodiments, the sensor (or a device coupled to the sensor) may be configured to administer a stimulus to the user when an audio event occurs or the audio event reaches a certain threshold (e.g., the degree of exhale). For example, the stimulus could be a shock, vibration, scent, sound, or flavor. Those skilled in the art will appreciate that one stimulus could be used to train the user to make thorough exhalation while another stimulus could train the user to take deep breaths. Any number of stimuli may be applied to the user with one or more sensors.

Figure 7:
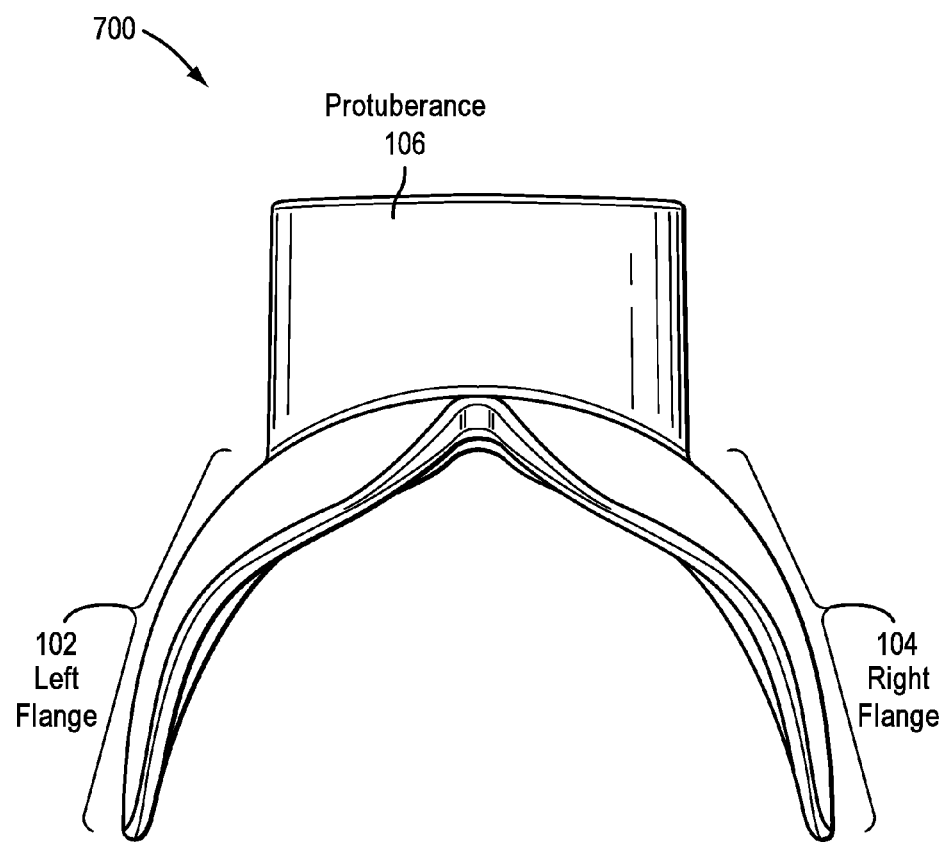
FIG. 7 is a bottom view of the exemplary breathing assistance device.

FIG. 7 is a bottom view 700 of the exemplary breathing assistance device 100. The breathing assistance device 100 may also be used to assist in medical procedures or when breathing becomes important in a medical emergency. In one example, the breathing assistance device 100 is placed in the user's mouth by an assistant or medical specialist. The device may be inserted into the mouth of a user who is unconscious to maintain an open airway. The breathing assistance device 100 may also be modified to hold the user's tongue during epileptic seizures.

Figure 8:
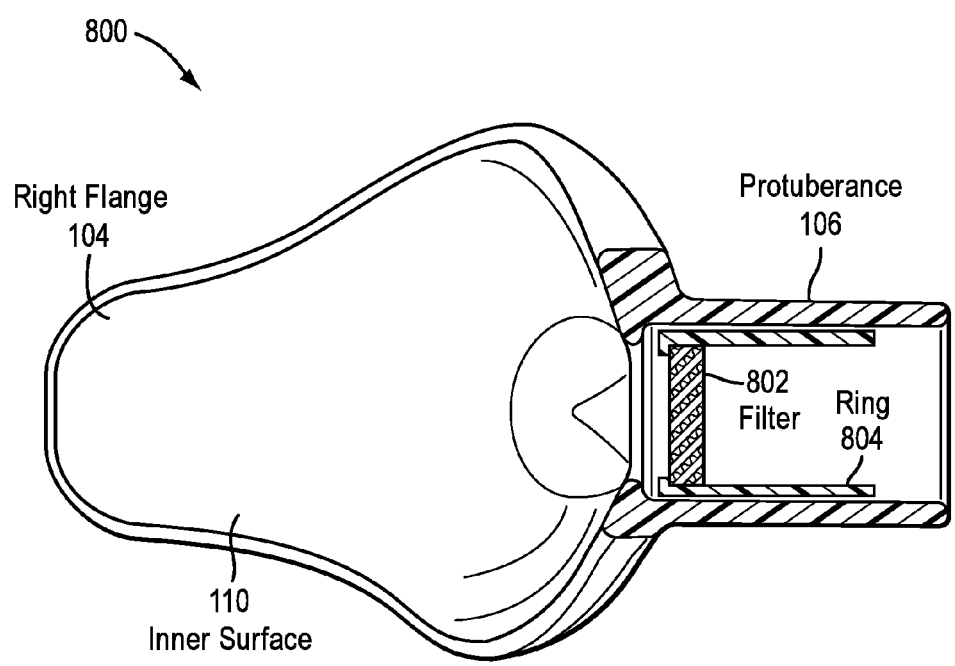
FIG. 8 is a right cross-section view of the exemplary breathing assistance device.

FIG. 8 is a right cross-section view 800 of the exemplary breathing assistance device. The cross-section view 800 depicts the right flange 102, the inner surface 110, and the protuberance 106. Inside the protuberance 106, a filter 802 and ring 804 is depicted. Those skilled in the art will appreciate that the cross-section view 800 depicts the a cross-section of the ring 804. The ring 804 is an enclosure (e.g., such as a ring or oval) may be substantially the shape of the inside of the protuberance 106. In some embodiments, the ring 804 fits within the protuberance 106 and holds the filter 802.

In various embodiments, the user manually inserts the ring 804 and filter 802 within the protuberance 106. In one example, the ring 804 and filter 802 may be removed and another ring 804 and filter 802 may be placed within the protuberance 106. In other embodiments, the ring 804 and filter 802 is designed within the breathing assistance device 100 and is not inserted by the user.

The filter 802 may be any filter of any material as discussed herein. Although the filter 802 is depicted as being at one end of the ring 804, those skilled in the art will appreciate that the filter 802 may be any size any may fill the ring 802.

Figure 9:
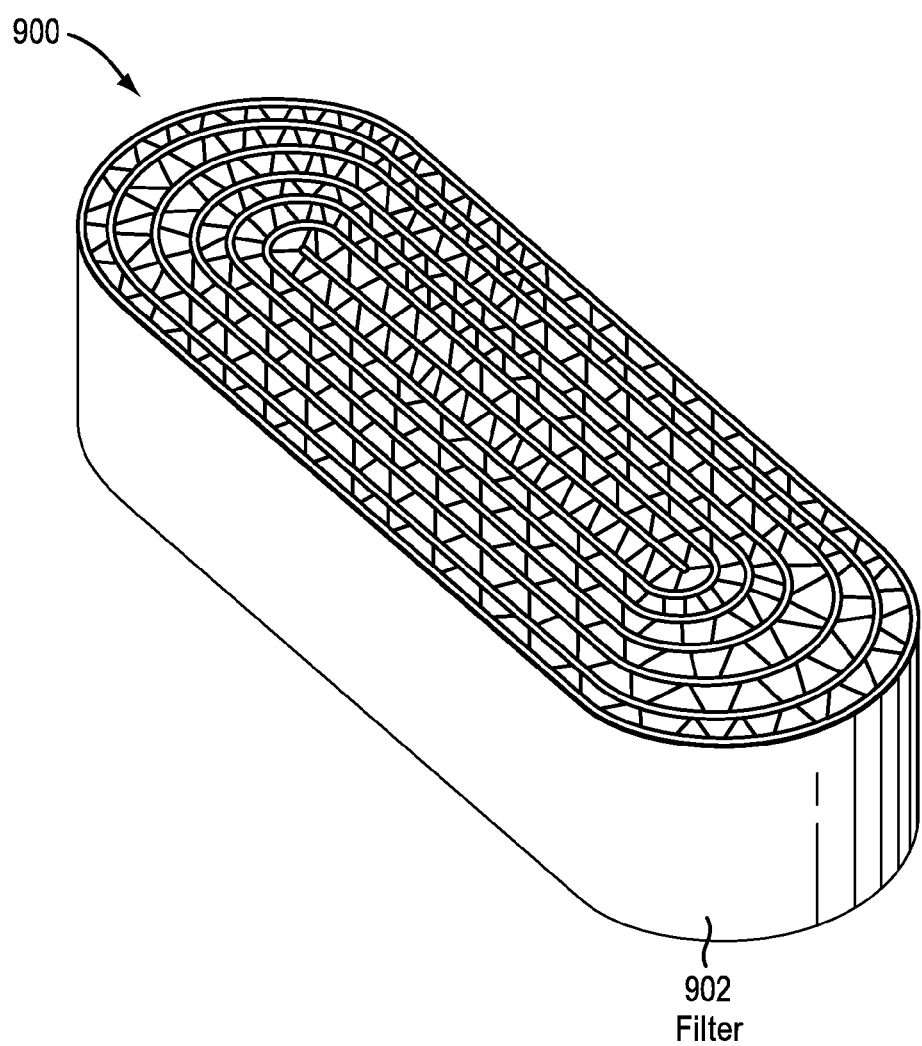
FIG. 9 is view of a filter of the exemplary breathing assistance device.

FIG. 9 is view 900 of a filter 902 of the exemplary breathing assistance device. The filter 902 is a roll of material that may be configured to fit within the protuberance 106 of the breathing assistance device 100. In one example, the filter 902 comprises a strip of corrugated paper covered in shellac. The strip of paper is rolled to create the filter 902. The filter 902 may then be inserted within the protuberance 106 and/or the ring 804 (see FIG. 8).

In some embodiments, a variety of different size strips and different materials may be available to the user. The user may select a strip size and/or material based on their needs such as lung strength. A longer strip of material may be rolled to create a denser filter 902 thereby increasing the air resistance properties of the filter. A shorter strip of material may be rolled to create a less dense filter 902. Further, different materials may provide for different air resistance properties.

In various embodiments, a user may purchase the breathing assistance device 100 from a store and receive a variety of filter materials. The filter materials may include filters and/or strips of different materials. The strips may be of different lengths. In some embodiments, the breathing assistance device 100 may include a chart which indicates which filter or filter materials is appropriate for the user. In one example, the chart identifies one or more appropriate filters based on lung strength. The chart may indicate that a certain user with a specific lung strength should tear a strip of material from a perforated page and roll the strip into the desired term. The user may then push the rolled material (e.g., the filter) into the protuberance 106 of the breathing assistance device 100. The chart may give an indication on how long the strip should be, how wide the strip should be, and/or the material of the strip. In some embodiments, different filters may be folded or rolled in different ways. In one example, the material for a filter may be inappropriate for rolling so folding the material bay be suitable. In another example, different ways to roll and/or fold the material may give the filter different air resistant properties that may be desirable based on the user.

The breathing assistance device 100 could be used for other medical uses and treat specific medical symptoms. Other medical uses may include, but are not limited to, endoscopy, tooth whitening, drug delivery, claustrophobia, any disease or health condition that causes shallow breathing including old age, dementia, epilepsy (with modifications to hold tongue in place during seizure).

In various embodiments, the breathing assistance device 100 comprises a breathing tube that substantially protrudes down the user's throat to improve airflow during inspiratory gasp response breathing. The breathing assistance device 100 may also be used in combination with low-pressure oxygen that could be injected into the breathing airway.

It should be noted that the breathing assistance device 100 may not be limited to sleeping or medical emergencies. In some embodiments, the breathing assistance device 100 may also be used in conjunction with any activity. In one example, the user may wish to improve oxygen flow and use the breathing assistance device 100 while preparing for an athletic event, such as swimming, boxing, football, rugby, speed skiing, or race car driving. In some sports, the user may be wearing a helmet or mouth piece that diminishes the amount of oxygen that the athlete can inhale or exhale because of a protective mouth guard. The mouth guard may be replaced with the breathing assistance device 100 or reconfigured to include the protuberance 106 and air passage 108. The protuberance 106 and air passage 108 may also be extended. In one example, while preparing for an athletic event, such as swimming, boxing, football, rugby, speed skiing, a user places the breathing assistance device 100 in their mouth. In this example the breathing tube is extended so that air can be drawn from outside of a helmet or other obstruction. This may reduce the amount of moisture within the helmet environment during the athletic activity.

In another example, the user may use the breathing assistance device 100 while performing work activity such as welding or painting. In this example, the breathing tube may be extended so that air can be drawn from outside of an air filter or other obstruction. This may allow the user to breathe fresh air, even though the air in their immediate environment contained pollutants.

In various embodiments, the user may use the breathing assistance device 100 while engaging in a high-stress activity. The breathing assistance device 100 may monitor the user's breathing patterns and adjust the pressure in the breathing airway to encourage the user to take breaths at regular intervals. The stimulus could also encourage deeper breathing by applying negative pressure to the breathing airway while the user is exhaling and positive pressure when the user is inhaling. Further, the breathing assistance device 100 may be used by the elderly to increase airflow, increase strength, and possibly reduce dementia.

The present invention is described above with reference to exemplary embodiments. It will be apparent to those skilled in the art that various modifications may be made and other embodiments can be used without departing from the broader scope of the present invention. Therefore, these and other variations upon the exemplary embodiments are intended to be covered by the present invention.

The invention claimed is:

1. A device for relieving sleep apnea, the device comprising:
    right and left flanges comprising an inner surface and an outside surface, the flanges configured to be placed in a user's mouth, wherein at least a portion of the flanges are in front of teeth of the user; and
    a protuberance extending from the outside surface of the flanges, the protuberance defining an air passage that passes through the flanges and that comprises a filter assembly comprising a filter, wherein the filter is positioned entirely within the protuberance, wherein a filter ring that is positioned entirely within the protuberance is configured to restrain the filter entirely in the protuberance, wherein the filter can be separated from the filter ring and both the filter ring and filter can be removed from the protuberance; and
    wherein the filter provides a 5-10% greater air resistance to cause a reduction in air flow capacity less than the user's natural breathing capacity to thereby create an amount of aerodynamic drag in the filter assembly, which in turn increases esophageal pressure which causes the sinuses to release nitric oxide, which in turn causes the lungs to expand to facilitate respiration and to relieve sleep apnea.

2. The device of claim 1, wherein the right and left flanges are canted.

3. The device of claim 1, wherein the protuberance comprises one or more holes to allow saliva to flow out of the user's mouth.

4. The device of claim 1, wherein the device is formed to create a frenulum gap along a y axis of the breathing assistance device, wherein the frenulum gap is configured to allow a user's frenulum to be in frenulum gap.

5. The device of claim 1, wherein the protuberance extends from the outside surface at an angle.

6. The device of claim 1, wherein the right flange and left flange comprises edges which are configured to contact gums of the user.

7. The device of claim 1 wherein the protuberance further comprises at least one valve that collapses or expands when air flows in a specific direction to constrict air flow when the user inhales or exhales.

8. The device of claim 1 wherein the filter may comprise one or more holes that allow saliva to be forced out by air pressure.

9. The device of claim 1, wherein the filter further comprises a valve that allows adjustment to the airflow through the filter.

10. The device of claim 1, wherein the device is coupled to a monitoring device configured to detect when the user's blood oxygenation level drops below a configured level.

* * * * *